United States Patent
Katz

(10) Patent No.: US 10,856,827 B2
(45) Date of Patent: **\*Dec. 8, 2020**

(54) UNMAPPED REGION VISUALIZATION

(71) Applicant: BIOSENSE WEBSTER (ISRAEL), LTD., Yokneam (IL)

(72) Inventor: Natan Sharon Katz, Kiryat Bialik (IL)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 962 days.

This patent is subject to a terminal disclaimer.

(21) Appl. No.: 15/439,013

(22) Filed: Feb. 22, 2017

(65) Prior Publication Data
US 2017/0156595 A1    Jun. 8, 2017

Related U.S. Application Data

(63) Continuation of application No. 13/964,377, filed on Aug. 12, 2013, now Pat. No. 9,775,578.

(51) Int. Cl.
*A61B 6/00* (2006.01)
*G01R 33/34* (2006.01)
(Continued)

(52) U.S. Cl.
CPC ............ *A61B 6/5205* (2013.01); *A61B 5/042* (2013.01); *A61B 5/06* (2013.01); *A61B 5/062* (2013.01);
(Continued)

(58) Field of Classification Search
None
See application file for complete search history.

(56) References Cited

U.S. PATENT DOCUMENTS 5,391,199 A    2/1995   Ben-Haim
5,443,489 A    8/1995   Ben-Haim
(Continued)

FOREIGN PATENT DOCUMENTS

AU    2004273587 B2    3/2005
CN    101219061 A      7/2008
(Continued)

OTHER PUBLICATIONS

European Search Report for corresponding Application No. EP14180558, dated Jan. 5, 2015.
(Continued)

*Primary Examiner* — Jonathan Cwern
(74) *Attorney, Agent, or Firm* — Notaro, Michalos & Zaccaria P.C.

(57) ABSTRACT

A method, including capturing, from an imaging system, a three-dimensional (3D) image of a body cavity, and using the captured 3D image to construct a simulated surface of the body cavity. A probe having a location sensor is inserted into the body cavity, and in response to multiple location measurements received from the location sensor, multiple positions are mapped within respective regions of the body cavity so as to generate respective mapped regions of the simulated surface. Based on the simulated surface and the respective mapped regions, one or more unmapped regions of the simulated surface are delineated, and the simulated surface of the body cavity is configured to indicate the delineated unmapped regions.

20 Claims, 3 Drawing Sheets

(51) Int. Cl.
*A61B 6/03* (2006.01)
*G01R 33/48* (2006.01)
*A61B 5/00* (2006.01)
*A61B 5/06* (2006.01)
*A61B 5/042* (2006.01)
*A61B 34/20* (2016.01)
*A61B 34/00* (2016.01)
*A61B 90/00* (2016.01)
*G01R 33/28* (2006.01)
*A61B 5/055* (2006.01)
*A61B 17/00* (2006.01)

(52) U.S. Cl.
CPC ............ *A61B 5/068* (2013.01); *A61B 5/6852* (2013.01); *A61B 5/742* (2013.01); *A61B 5/743* (2013.01); *A61B 6/032* (2013.01); *A61B 6/4057* (2013.01); *A61B 6/466* (2013.01); *A61B 6/503* (2013.01); *A61B 34/20* (2016.02); *A61B 34/25* (2016.02); *A61B 90/37* (2016.02); *G01R 33/285* (2013.01); *G01R 33/34084* (2013.01); *G01R 33/48* (2013.01); *G01R 33/4812* (2013.01); *A61B 5/0044* (2013.01); *A61B 5/055* (2013.01); *A61B 2017/00053* (2013.01); *A61B 2034/2051* (2016.02); *A61B 2034/254* (2016.02); *A61B 2090/064* (2016.02); *A61B 2090/065* (2016.02); *A61B 2090/374* (2016.02)

(56) References Cited

U.S. PATENT DOCUMENTS

| | | | |
|---|---|---|---|
| 5,558,091 | A | 9/1996 | Acker et al. |
| 5,899,860 | A | 5/1999 | Pfeiffer et al. |
| 5,944,022 | A | 8/1999 | Nardella et al. |
| 5,983,126 | A | 11/1999 | Wittkampf |
| 6,172,499 | B1 | 1/2001 | Ashe |
| 6,177,792 | B1 | 1/2001 | Govari et al. |
| 6,456,864 | B1 | 9/2002 | Swanson et al. |
| 6,574,498 | B1 | 6/2003 | Gilboa |
| 6,690,963 | B2 | 2/2004 | Ben-Haim et al. |
| 6,788,967 | B2 | 9/2004 | Ben-Haim et al. |
| 8,103,338 | B2 | 1/2012 | Harlev et al. |
| 8,208,998 | B2 | 6/2012 | Beatty et al. |
| 9,775,578 | B2 * | 10/2017 | Katz ...................... A61B 6/503 |
| 2003/0013957 | A1 * | 1/2003 | Bjaerum ............. G01S 7/52071 600/437 |
| 2006/0089625 | A1 | 4/2006 | Voegele et al. |
| 2007/0016007 | A1 | 1/2007 | Govari et al. |
| 2007/0299351 | A1 | 12/2007 | Harlev et al. |
| 2008/0190438 | A1 | 8/2008 | Harlev et al. |
| 2009/0093806 | A1 | 4/2009 | Govari et al. |
| 2009/0138007 | A1 | 5/2009 | Govari et al. |
| 2009/0281439 | A1 | 11/2009 | Harlev et al. |
| 2010/0079158 | A1 | 4/2010 | Bar-Tal et al. |
| 2010/0268059 | A1 | 10/2010 | Ryu et al. |
| 2010/0312094 | A1 | 12/2010 | Guttman et al. |
| 2011/0021903 | A1 | 1/2011 | Strommer et al. |
| 2013/0184569 | A1 | 7/2013 | Strommer et al. |

FOREIGN PATENT DOCUMENTS

| | | |
|---|---|---|
| CN | 101449985 A | 6/2009 |
| CN | 102085117 A | 6/2011 |
| CN | 102551667 A | 7/2012 |
| DE | 10340544 A1 | 3/2005 |
| EP | 2075763 A1 | 7/2009 |
| EP | 2449962 A1 | 5/2012 |
| JP | 2009136679 A | 6/2009 |
| JP | 2010528683 A | 8/2010 |
| WO | 2008138009 A1 | 11/2008 |
| WO | 2009134605 A2 | 11/2009 |

OTHER PUBLICATIONS

Chinese first Office Action and Search Report for corresponding Chinese application No. 201410393322.7, dated Jul. 2, 2018.
Gallagher J et al: "Techniques of intraoperative electrophysiologic mapping", American Journal of Cardiology, Cahners Publishing Co., Newton, MA, US, vol. 49, No. 1, Jan. 1, 1982 (Jan. 1, 1982), pp. 221-240.
Extended European Search Report for corresponding European patent application No. EP 14180558.0, dated Jan. 5, 2015.
Japanese Office Action for corresponding Japanese application No. JP 2014-163620, dated Apr. 25, 2018.

* cited by examiner

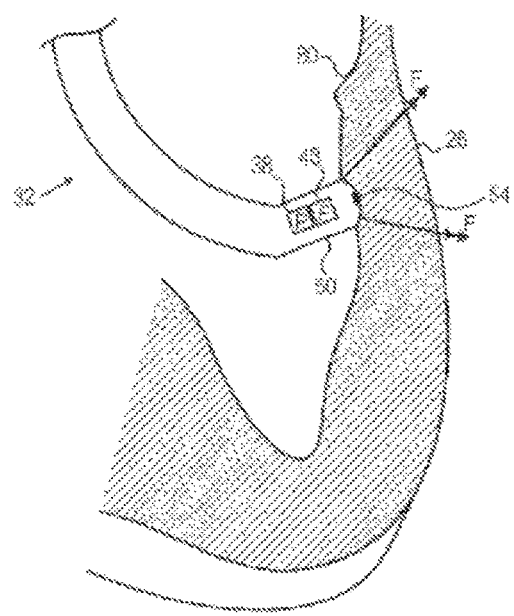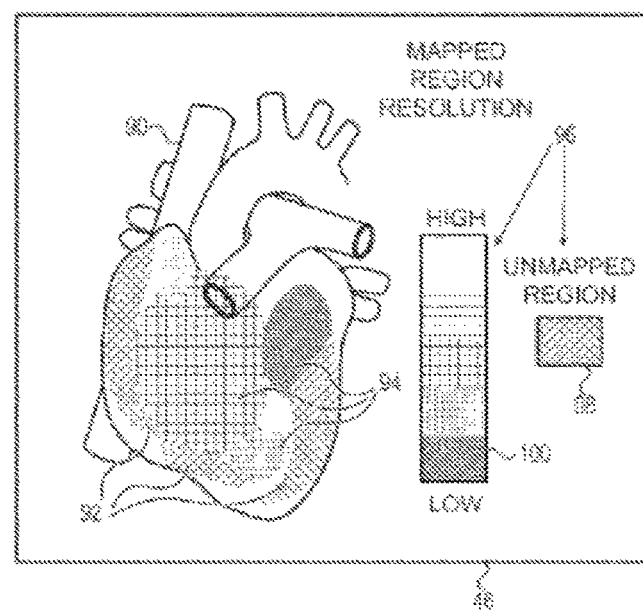
FIG. 3
FIG. 4

UNMAPPED REGION VISUALIZATION

FIELD OF THE INVENTION

The present invention relates generally to medical imaging, and specifically to using a medical probe to map a surface of a cavity of a body organ.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Patent Application 2007/0016007, to Govari et al., whose disclosure is incorporated herein by reference, describes a hybrid magnetic-based and impedance-based position sensing system. The system includes a probe adapted to be introduced into a body cavity of a subject.

U.S. Pat. No. 6,574,498, to Gilboa, whose disclosure is incorporated herein by reference, describes a system for determining the position of a work piece within a cavity of an opaque body. The system claims to use a transducer that interacts with a primary field, and several transducers that interact with a secondary field.

U.S. Pat. No. 5,899,860, to Pfeiffer, et al., whose disclosure is incorporated herein by reference, describes a system for determining the position of a catheter inside the body of a patient. A correction function is determined from the difference between calibration positions derived from received location signals and known, true calibration positions, whereupon catheter positions, derived from received position signals, are corrected in subsequent measurement stages according to the correction function.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention a method, including capturing, from an imaging system, a three-dimensional (3D) image of a body cavity, constructing, using the captured 3D image, a simulated surface of the body cavity, inserting a probe having a location sensor into the body cavity, mapping multiple positions within respective regions of the body cavity, in response to multiple location measurements received from the location sensor, so as to generate respective mapped regions of the simulated surface, delineating, based on the simulated surface and the respective mapped regions, one or more unmapped regions of the simulated surface, and configuring the simulated surface of the body cavity to indicate the delineated unmapped regions.

In some embodiments, the imaging system may be selected from a list including a magnetic resonance imaging system and a computed tomography system. In additional embodiments, the method may include presenting an image of the configured simulated surface on a display, and in further embodiments the image may be selected from a list including at least one of the one or more unmapped regions and the respective mapped regions.

In some embodiments, the probe may include an intracardiac catheter, and the body cavity may include a chamber of a heart. In additional embodiments, the catheter may include a force sensor positioned at a distal end of the catheter, and mapping a given position may include receiving a given location measurement upon receiving, from the force sensor, a force measurement indicating a contact between the distal end and endocardial tissue in the chamber.

In some embodiments, configuring the simulated surface may include associating a visual design with the unmapped regions, and overlaying the visual design on the unmapped regions of the simulated surface. In additional embodiments, the visual design may be selected from group including a shading, an intensity and a pattern.

In some embodiments, delineating the one or more mapped regions may include subtracting the respective mapped regions from the simulated surface. In additional embodiments, the location sensor may include an electrode attached to the probe, and mapping the multiple positions may include measuring impedances to a current transmitted through the electrode. In alternative embodiments, the location sensor may include a magnetic field sensor, and mapping the multiple positions may include measuring magnetic fields using the magnetic field sensor.

There is also provided, in accordance with an embodiment of the present invention an apparatus, including a probe, configured for insertion into a body cavity of a patient and including a location sensor for measuring a position of a distal end of the probe inside the body cavity, and a processor configured to capture, from an imaging system, a three-dimensional (3D) image of the body cavity, to construct, using the captured 3D image, a simulated surface of the body cavity, to map, while inserting the probe into the body cavity, multiple positions within respective regions of the body cavity, in response to multiple location measurements received from the location sensor, so as to generate respective mapped regions of the simulated surface, to delineate, based on the simulated surface and the respective mapped regions, one or more unmapped regions of the simulated surface, and to configure the simulated surface of the body cavity to indicate the delineated unmapped regions.

There is further provided, in accordance with an embodiment of the present invention, a computer software product operated in conjunction with a probe that is configured for insertion into a body cavity of a patient and includes a location sensor for measuring a location of a distal end of the probe inside the body cavity, the product including a non-transitory computer-readable medium, in which program instructions are stored, which instructions, when read by a computer, cause the computer to capture, from an imaging system, a three-dimensional (3D) image of a body cavity, to construct, using the captured 3D image, a simulated surface of the body cavity, to map, while, inserting the probe into the body cavity, multiple positions within respective regions of the body cavity, in response to multiple location measurements received from the location sensor, so as to generate respective mapped regions of the simulated surface, to delineate, based on the simulated surface and the respective mapped regions, one or more unmapped regions of the simulated surface, and to configure the simulated surface of the body cavity to indicate the delineated unmapped regions.

BRIEF DESCRIPTION OF THE DRAWINGS

The disclosure is herein described, by way of example only, with reference to the accompanying drawings, wherein:

FIG. 3 is a schematic detail view showing a distal tip of a catheter in contact with endocardial tissue of the cardiac chamber, in accordance with an embodiment of the present invention; and FIG. 4 is a schematic pictorial illustration of an image presented on the catheter-tissue contact visualization system, in accordance with an embodiment of the present invention.

DETAILED DESCRIPTION OF EMBODIMENTS

Overview

Physiological or anatomical mapping procedures typically create a map comprising map points collected from an electroanatomical mapping system. Each map point comprises a respective coordinate within a body cavity, and possibly a physiological property collected by a medical probe at the respective coordinate. While mapping a body cavity such as a chamber of a heart, the map may have resolutions that vary from region to region. The variation can be based on the number of measurements collected for a particular region used to generate the map.

Embodiments of the present invention provide methods and systems for visualizing unmapped regions of the body cavity. In some embodiments, the unmapped regions may be determined by subtracting the mapped regions from an image of the body cavity that has been pre-acquired using, for example, magnetic resonance imaging or computer tomography. By conveying visual feedback delineating non-mapped regions of the body cavity, embodiments of the present invention can provide, to a medical professional performing a medical procedure, a visual guide indicating any unmapped regions of the body cavity that need to be mapped during the medical procedure.

System Description

Figure 1:
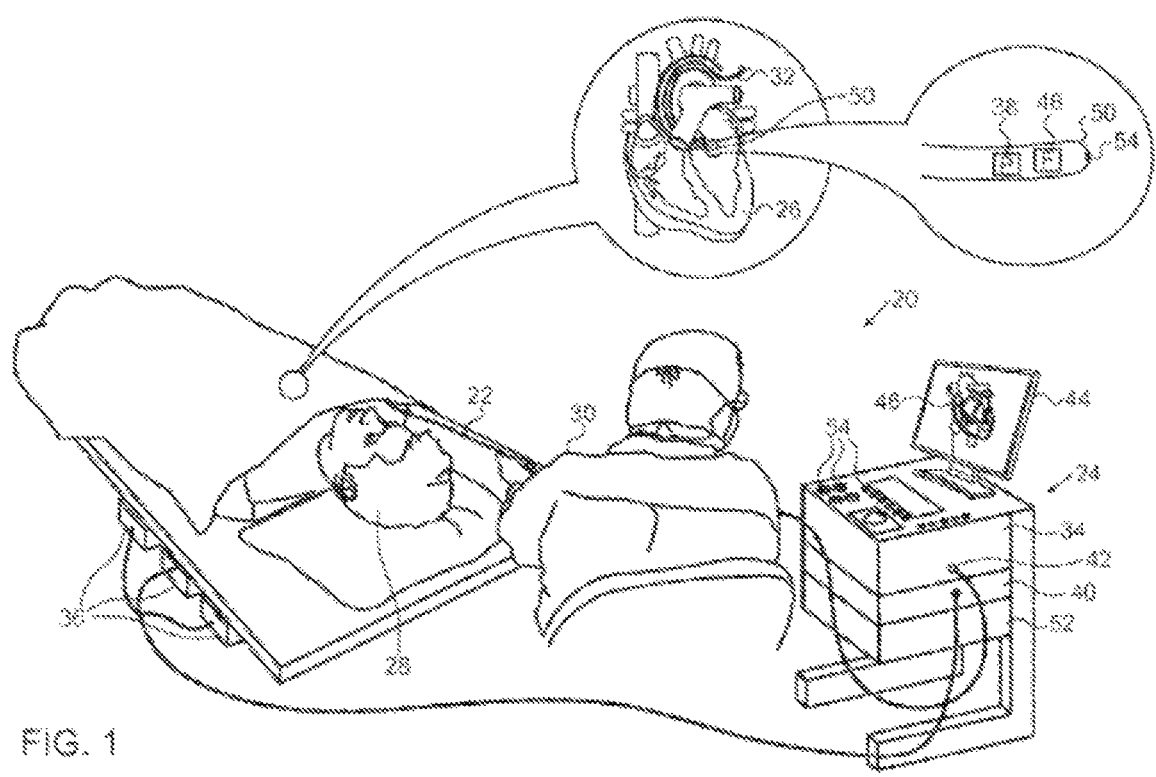
FIG. 1 is a schematic pictorial illustration of a catheter-tissue contact visualization system for a force-sensing catheter, in accordance with an embodiment of the present invention.

FIG. 1 is a schematic, pictorial illustration of an intracardiac mapping system 20 that implements visualization of catheter-tissue contact, in accordance with an embodiment of the present invention. System 20 comprises a probe 22, such as an intracardiac catheter, and a control console 24. In embodiments described hereinbelow, it is assumed that probe 22 is used for diagnostic or therapeutic treatment, such as for mapping electrical potentials in a heart 26 of a patient 28. Alternatively, probe 22 may be used, mutatis mutandis, for other therapeutic and/or diagnostic purposes in the heart or in other body organs.

An operator 30 inserts probe 22 through the vascular system of patient 28 so that a distal end 32 of probe 22 enters a chamber of heart 26. Console 24 typically uses magnetic position sensing to determine position coordinates of distal end inside heart 26. To determine the position coordinates, a driver circuit 34 in console 24 drives field generators 36 to generate magnetic fields within the body of patient 28. Typically, field generators 36 comprise coils, which are placed below the patient's torso at known positions external to patient 28. These coils generate magnetic fields in a predefined working volume that contains heart 26. A magnetic field sensor (also referred to herein as location sensor 38) within distal end 32 of probe 22 generates electrical signals in response to these magnetic fields. A signal processor 40 processes these signals in order to determine the position coordinates of distal end 32, typically including both location and orientation coordinates. The method of position sensing described hereinabove is implemented in the above-mentioned CARTO™ system and is described in detail in the patents and patent applications cited above.

Location sensor 38 transmits a signal to console 24 that is indicative of the location coordinates of distal end 32. Location sensor 38 may comprise one or more miniature coils, and typically comprises multiple coils oriented along different axes. Alternatively, location sensor 38 may comprise either another type of magnetic sensor, or position transducers of other types, such as impedance-based or ultrasonic location sensors. Although FIG. 1 shows a probe with a single location sensor, embodiments of the present invention may utilize probes with more than one location sensor.

In an alternative embodiment, the roles of location sensor 38 and magnetic field generators 36 may be reversed. In other words, driver circuit 34 may drive a magnetic field generator in distal end 32 to generate one or more magnetic fields. The coils in generator 36 may be configured to sense the fields and generate signals indicative of the amplitudes of the components of these magnetic fields. Processor 40 receives and processes these signals in order to determine the position coordinates of distal end 32 within heart 26.

Although in the present example system 20 measures the position of distal end 32 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

In embodiments described herein, processor 40 is configured to collect image data from a medical imaging system (not shown) such as a magnetic resonance imaging (MRI) system, or a computed tomography (CT) system, or a probe mapping system such as the CARTO™ mapping system produced by Biosense Webster Inc., of Diamond Bar, Calif. As described hereinbelow, processor 40 uses the image data to construct a simulated surface of the cardiac chamber in question.

Processor 40 typically comprises a general-purpose computer, with suitable front end and interface circuits for receiving signals from probe 22 and controlling the other components of console 24. Processor 40 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 40 may be carried out by dedicated or programmable digital hardware components.

An input/output (I/O) interface 42 enables console 24 to interact with probe 22. Based on the signals received from probe 22 (via interface 42 and other components of system 20), processor 40 drives a display 44 to present operator 30 with an image 46 showing the position of distal end 32 in the patient's body, as well as status information and guidance regarding the procedure that is in progress.

Probe 22 also comprises a force sensor 48 contained within distal end 32. Force sensor 48 measures a force applied by a distal tip 50 of probe 22 to the endocardial tissue of heart 26 by generating a signal to the console that is indicative of the force exerted by the distal tip on the endocardial tissue. In one embodiment, the force sensor may comprise a magnetic field transmitter and receiver connected by a spring in distal end 32, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

Additionally or alternatively, system 20 may comprise an automated mechanism (not shown) for maneuvering and operating probe 22 within the body of patient 28. Such mechanisms are typically capable of controlling both the longitudinal motion (advance/retract) of probe 22 and transverse motion (deflection/steering) of distal end 32 of the probe. In such embodiments, processor 40 generates a control input for controlling the motion of probe 22 based on the signals provided by the magnetic field sensor in the probe.

In order to map the cardiac chamber in question, operator 30 advances probe 22 so that distal tip 50 engages endocardial tissue at multiple locations, and processor 40 "registers" the multiple locations on the simulated surface produced from the image data. Thus, the system collects multiple map points, with each map point comprising a coordinate on the inner chamber surface. In embodiments of the present invention, processor 40 can use signals received from force sensor 48 to detect when distal tip 50 is in contact with the endocardial tissue.

In alternative embodiments, probe 22 may comprise an electrode 54 coupled to the distal end and configured to function as an impedance-based position transducer. Additionally or alternatively, electrode 54 can be configured to measure a certain physiological property (e.g., the local surface electrical potential) at each of the multiple locations. In some embodiments, system 20 can correlate the position measurements and the electrical potential measurements. In other words, system 20 can collect multiple map points, with each map point comprising a coordinate on the inner chamber surface and a respective physiological property measurement at this coordinate.

During the diagnostic treatment, processor 40 presents image 46 of the simulated surface, with the registered location measurements laid thereon (the fusion of the simulated surface and the location measurements is referred to herein as a map), to operator 30 on display 44, and stores data representing the image in a memory 52. Memory 52 may comprise any suitable volatile and/or non-volatile memory, such as random access memory or a hard disk drive. After collecting the image data, processor 40 applies an algorithm (e.g., a fast mapping process) to construct image 46. In the present embodiment, image 46 comprises a simulated 3D surface (e.g., a polygon mesh) of a surface of the cardiac chamber, which processor 40 presents as image 46 on display 44. In some embodiments, operator 30 can manipulate image 46 using one or more input devices 54.

Although FIG. 1 shows a particular system configuration, other system configurations can also be employed to implement embodiments of the present invention, and are thus considered to be within the spirit and scope of the present invention. For example, the methods described hereinbelow may be applied using position transducers of types other than the magnetic field sensor described above, such as impedance-based or ultrasonic location sensors. The term "position transducer" as used herein refers to an element mounted on probe 22 which causes console 24 to receive signals indicative of the coordinates of the distal end. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in therapeutic and diagnostic applications using not only catheters, but also probes of other types, both in the heart and in other body organs and regions.

Simulated Surface Visualization

Figure 2:
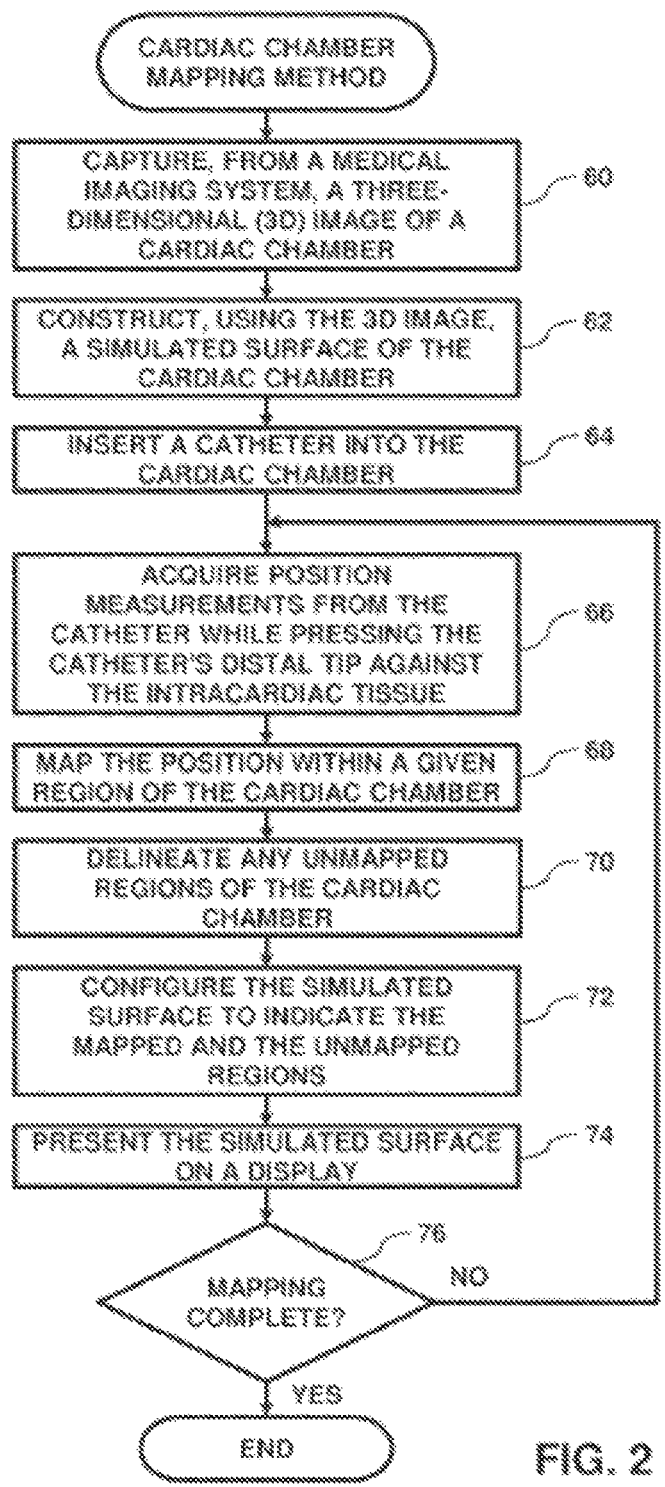
FIG. 2 is a flow diagram that schematically illustrates a method of mapping a cardiac chamber, in accordance with an embodiment of the present invention.

FIG. 2 is a flow diagram that schematically illustrates a method of mapping a chamber of heart 26, FIG. 3 is a schematic detail view showing distal tip 50 in contact with endocardial tissue 80 of heart 26, and FIG. 4 is a schematic pictorial illustration of image 46 comprising a simulated surface 90, in accordance with an embodiment of the present invention in accordance with an embodiment of the present invention. While the example shown in FIGS. 2-4 describe mapping a chamber of heart 26, embodiments of the present invention can be used to map any body cavity within patient 28.

In a capture step 60, processor 40 captures (i.e., receives) a three dimensional (3D) image of a chamber of heart 26, and in a construction step 62, the processor uses the 3D image to construct simulated surface 90 in memory 52. As described supra, processor 40 can collect the 3D image from a MRI or a CT system.

In an insertion step 64, operator 30 inserts probe 22 into a chamber of heart 26 (also referred to herein as the cardiac chamber), and advances the probe so that distal tip 50 engages endocardial tissue 80 and exerts force F on the endocardial tissue, as shown in FIG. 3. To verify contact between distal tip 50 and endocardial tissue, processor 40 receives force measurements from force sensor 48 that indicate force F. In an acquire step 66, while distal tip 50 presses against endocardial tissue 80, processor 40 automatically acquires location measurements from location sensor 38 indicating a current position of distal end 32.

In response to the location and the force measurements, processor 40, in a mapping step 68, maps the location measurement to a given region of the simulated surface. In operation, upon detecting distal tip 50 engaging endocardial tissue 80 at multiple locations, processor 40 can map each of the multiple locations to a corresponding region of the simulated surface without any intervention from the operator.

In a delineation step 70, the processor delineates any unmapped regions in the cardiac chamber. In addition to delineating one or more unmapped regions in the cardiac chamber, as processor 40 receives force and position measurements from probe 22, the processor can delineate respective mapped regions of the simulated surface.

In embodiments where processor 40 receives the location measurements from magnetic field sensor 38, the processor can map the received magnetic field measurements to corresponding locations on the simulated surface. In embodiments where processor 40 receives the location measurements from electrode 54, the location measurements comprising impedances to a current transmitted through the electrode, the processor can map the received impedance measurements to corresponding locations on the simulated surface. Additionally or alternatively, processor can use first location measurements received from magnetic field sensor to calibrate second location measurements received from electrode 54.

In some embodiments, processor 40 can delineate the unmapped region(s) by subtracting the respective mapped regions from the simulated surface. Additionally, processor 40 can delineate mapping resolutions for different mapped regions of the simulated surface. In embodiments of the present invention a given mapping resolution for a given region comprises a number of positions mapped in the given region using embodiments described hereinabove. In other words, if the cardiac chamber comprises first and second regions having similarly sized surface areas, and the first region has ten positions mapped and the second region has six positions mapped, then the mapping resolution of the first region is higher than the mapping resolution of the second region.

In a configuration step 72, processor 40 configures simulated surface 90 to indicate the mapped and the unmapped regions of the cardiac chamber, and in a presentation step 74, the processor presents, on display 44, image 46 comprising the simulated surface. In the example shown in FIG. 4, image 46 comprises both mapped regions 92 and unmapped regions 94. In alternative embodiments, image 46 may comprise either mapped regions 92 or unmapped regions 94 (i.e., one or the other).

To configure simulated surface 90, processor 40 can associate a first visual design with the unmapped regions, and overlay the first visual design on the unmapped regions of the simulated surface. Additionally, processor 40 can associate a second visual design with the mapped regions, and overlay the second visual design on the mapped regions of the simulated surface. In some embodiments, the visual design may comprise a shading or an intensity. In alternative embodiments, the visual design may comprise or visual patterns 98 and 100, as shown in FIG. 4.

Additionally, processor 40 can present a legend 96 that details visual patterns 98 and 100 that the processor can use when presenting the mapped and the unmapped regions. In the example shown in FIG. 4, legend 96 comprises unmapped pattern and multiple mapped patterns 100, wherein each mapping resolution (or each range of mapping resolutions) has a respective mapped pattern 100. In other words, while presenting simulated surface 90, processor 40 overlays unmapped pattern 98 on the unmapped regions and overlays the respective mapped pattern 100 for each of the mapped regions, thereby conveying visual feedback to operator 30 for the procedure that is in progress.

Finally, in a comparison step 76, if additional locations in the cardiac chamber need to be mapped, then operator 30 repositions catheter 22 and the method continues with step 66. However, if no additional locations are needed, then mapping the cardiac chamber is complete, and the method ends.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus comprising:
   a display; a probe configured for insertion into a body cavity of a patient and comprising a location sensor for measuring a position of a distal end of the probe inside the body cavity; and
   a processor; wherein the apparatus is configured:
   to receive a three-dimensional image of at least part of a body cavity, the three-dimensional image comprising an image from one of a magnetic resonance imaging system and a computed tomography system;
   to construct a simulated surface of at least part of said body cavity using said three-dimensional image, and to show the simulated surface on the display;
   after constructing said simulated surface, to receive signals from the location sensor of the probe, the signals comprising a series of locations of the probe inside said body cavity;
   when the probe is located inside said body cavity, to map at least a portion of the body cavity corresponding to said simulated surface, the mapping process comprising:
   (i) when a tip of the probe is positioned against a body cavity tissue, determining that the tip is positioned against the body cavity tissue; and then
   (ii) determining a position of the tip of the probe against the body cavity tissue using the location sensor in the probe; and then
   (iii) mapping said position of the tip of the probe against the body cavity tissue with respect to the simulated surface, and visually marking said position of the tip of the probe as a mapped region of the simulated surface on the display by overlaying one of a plurality of different mapped visual designs on a corresponding area of the simulated surface,
   (iii) a. wherein mapped regions remain marked with one of said plurality of mapped visual designs at least until completion of the mapping process;
   (iii) b. wherein areas of the simulated surface which remain unmapped are visually indicated as unmapped by overlaying a first visual design on corresponding areas of the simulated surface unless and until the unmapped areas are mapped; and (iii) c. wherein the apparatus is configured to perform said mapping and visual marking steps automatically in response to the probe tip being positioned against the body cavity tissue; and (iv) repeating steps (i)-(iii) a plurality of times when the tip of the probe is located in a series of different positions in the body cavity with the tip of the probe positioned against body cavity tissue; the apparatus being further configured so that when the apparatus performs said mapping process:

at least some regions of the simulated surface which have been visually marked as being mapped on the display during said mapping process are further modified during the course of the mapping process to visually indicate changing mapping resolution as additional tip positions are mapped;

mapping resolution corresponds to a quantity of different positions in a region of the simulated surface which have been mapped by the mapping process; and said plurality of mapped visual designs comprise a plurality of visually distinguishable mapping patterns on the display, each corresponding to different respective mapping resolutions.

2. The apparatus according to claim 1, the apparatus being further configured to present a legend on the display, the legend comprising the first visual design and the plurality of mapped visual designs, the plurality of mapped visual designs comprising a range of mapping patterns corresponding to different mapping resolutions.

3. The apparatus of claim 1, the apparatus being further configured to simultaneously show on the display:

areas of the simulated surface having the first visual design, indicating unmapped areas; areas of the simulated surface having a mapped visual design (x) indicating mapped areas; and areas of the simulated surface having a different mapped visual design (y) indicating mapped areas which have a different mapping resolution than said area having said mapped visual design (x).

4. The apparatus of claim 3, the apparatus being further configured so that when the mapping process is performed:

when the tip of the probe is located in a different second position in the body cavity where the tip is positioned against body cavity tissue, and wherein a corresponding portion of the simulated surface has previously been marked as mapped on the display using a mapped visual design (x) indicating a first mapping resolution; then in said corresponding portion of the simulated surface, the mapped visual design (x) indicating the first mapping resolution is replaced with the different mapped visual design (y), the different mapped visual design (y) indicating a different and higher mapping resolution than mapped visual design (x).

5. The apparatus of claim 1:
wherein the probe is an intracardiac catheter adapted for use inside a heart.

6. The apparatus of claim 1:
wherein the probe comprises a magnetic field sensor at the tip thereof.

7. The apparatus of claim 1:
wherein the apparatus comprises a table, and a plurality of field generators positioned under the table.

8. The apparatus of claim 1:
wherein the catheter comprises a force sensor; and wherein the apparatus is configured to determine that the tip of the catheter is positioned against the body cavity tissue in response to a force measurement from the force sensor during the mapping process.

9. The apparatus of claim 1, the apparatus being further configured to simultaneously show a plurality of different mapped visual designs on the display, and wherein said plurality of mapped visual designs differ from each other as to at least one of a shading, an intensity, and a pattern.

10. The apparatus of claim 1:
wherein the location sensor of the probe comprises an electrode, the electrode being configured to measure impedances to a current transmitted through the electrode.

11. The apparatus of claim 1, wherein the processor is functionally linked to one of a magnetic resonance imaging system, and a computed tomography system, and is configured to receive three-dimensional image data therefrom.

12. The apparatus of claim 1:
further comprising a non-transitory computer readable medium holding computer software instructions; wherein said computer software instructions, when executed by the processor, cause the apparatus to perform steps of said mapping process.

13. The apparatus of claim 1:
wherein the location sensor of the probe comprises at least one of: a plurality of coils oriented along different axes, an impedance-based location sensor, and an ultrasonic location sensor.

14. The apparatus of claim 1:
wherein the probe further comprises an electrode configured to measure a physiological property, and wherein the apparatus is adapted to save a plurality of physiological property measurements in correlation with a plurality of corresponding probe location coordinates on the body cavity.

15. A computer software product, operated in conjunction with an imaging arrangement comprising a computer processor, a display, and a probe, the probe being configured for insertion into a body cavity of a patient and comprising a location sensor for measuring a location of a distal end of the probe inside the body cavity, the software product comprising a non-transitory computer-readable medium, in which program instructions are stored, which program instructions, when read by a computer processor, cause the imaging arrangement to:

retrieve a three-dimensional image of at least part of a body cavity;

construct a simulated surface of at least part of said body cavity using said three-dimensional image, and show the simulated surface on the display;

after constructing said simulated surface, with the probe inside a body cavity, to map at least a portion of the body cavity corresponding to said simulated surface by a mapping process, the mapping process comprising:

(i) with a tip of the probe is positioned against a body cavity tissue, determining that the tip is positioned against the body cavity tissue;

(ii) determining a position of the tip of the probe against the body cavity tissue using the location sensor in the probe;

(iii) mapping said position of the tip of the probe while it is against the body cavity tissue with respect to the simulated surface, and visually marking said position of the tip of the probe as a mapped region of the simulated surface on the display by overlaying one of a plurality of different mapped visual designs on a corresponding area of the simulated surface, (iii) a. wherein mapped regions remain marked with one of said plurality of mapped visual designs at least until completion of the mapping process;

(iii) b. wherein areas of the simulated surface which remain unmapped are visually indicated as unmapped by overlaying a first visual design on corresponding areas of the simulated surface unless and until the unmapped areas are mapped; and (iii) c. wherein the apparatus is configured to perform said mapping and visual marking steps automatically in response to the probe tip being positioned against the body cavity tissue; and (iv) repeating steps (i)-(iii) a plurality of times when the tip of the probe is located in a series of different positions in the body cavity with the tip of the probe positioned against body cavity tissue; wherein when the mapping process is performed by the imaging arrangement according to said program instructions:

at least some regions of the simulated surface which have been visually marked as being mapped on the display during said mapping process are further modified during the course of the mapping process to visually indicate changing mapping resolution as additional tip positions are mapped;

mapping resolution corresponds to a quantity of different positions in a region of the simulated surface which have been mapped by the mapping process; and said plurality of mapped visual designs comprise a plurality of visually distinguishable mapping patterns on the display, each corresponding to different respective mapping resolutions.

16. The computer software product of claim 15, wherein when the mapping process is performed by the imaging arrangement according to said program instructions, the imaging arrangement simultaneously shows on the display:

areas of the simulated surface having the first visual design, indicating unmapped areas;

areas of the simulated surface having a mapped visual design (x) indicating mapped areas; and areas of the simulated surface having a different mapped visual design (y) indicating mapped areas which have a different mapping resolution than said area having said mapped visual design (x).

17. The computer software product of claim 15, wherein when the mapping process is performed by the imaging arrangement according to said program instructions:

when the tip of the probe is located in a different second position in the body cavity where the tip is positioned against body cavity tissue, and wherein a corresponding portion of the simulated surface has previously been marked as mapped on the display using a mapped visual design (x) indicating a first mapping resolution; then in said corresponding portion of the simulated surface, the mapped visual design (x) indicating the first mapping resolution is replaced with the different mapped visual design (y), the different mapped visual design (y) indicating a different and higher mapping resolution than mapped visual design (x).

18. The computer software product of claim 15:
wherein the software product is configured for use with a catheter which comprises a force sensor; and
wherein when the mapping process is performed by the imaging arrangement according to said program instructions, the imaging arrangement determines that the tip of the catheter is positioned against the body cavity tissue in response to receiving a force measurement from the force sensor during the mapping process.

19. A method, comprising:
capturing a three-dimensional image of at least part of a body cavity;
constructing a simulated surface of at least part of said body cavity using said three-dimensional image, and showing the simulated surface on a display;
inserting a probe having a location sensor into said body cavity;
with the probe inserted inside said body cavity, mapping at least a portion of said body cavity corresponding to said simulated surface, the mapping process comprising:

(i) moving a tip of the probe to a position in the body cavity where the tip is positioned against a body cavity tissue, and determining that the tip is positioned against the body cavity tissue;

(ii) determining a position of the tip of the probe while it is against the body cavity tissue using the location sensor in the probe;

(iii) mapping said position of the tip of the probe against the body cavity tissue with respect to the simulated surface, and visually marking said position of the tip of the probe as a mapped region of the simulated surface on the display by overlaying one of a plurality of different mapped visual designs on a corresponding area of the simulated surface, (iii) a. wherein mapped regions remain marked with one of said plurality of mapped visual designs at least until completion of the mapping process;

(iii) b. wherein areas of the simulated surface which remain unmapped are visually indicated as unmapped by overlaying a first visual design on corresponding areas of the simulated surface unless and until the unmapped areas are mapped; and (iii) c. wherein said mapping and visual marking takes place automatically in response to the probe tip being positioned against the body cavity tissue;

(iv) moving the tip of the probe to a different position in the body cavity where the tip is positioned against body cavity tissue; and (v) repeating steps (i)-(iv) a plurality of times; further:
wherein at least some regions of the simulated surface which have been visually marked as being mapped on the display during said mapping process are further modified during the course of the mapping process to visually indicate changing mapping resolution as additional tip positions are mapped;
wherein mapping resolution corresponds to a number of different positions in a region of the simulated surface which have been mapped by the mapping process; and
wherein said plurality of mapped visual designs comprise a plurality of visually distinguishable mapping patterns each corresponding to different respective mapping resolutions.

20. The method of claim 19, the method comprising simultaneously showing on the display:

(a) areas of the simulated surface having the first visual design, indicating unmapped areas;

(b) areas of the simulated surface having a mapped visual design (x) indicating mapped areas; and (c) areas of the simulated surface having a different mapped visual design (y) indicating mapped areas which have a different mapping resolution than said area having said mapped visual design (x);

the method further comprising moving the tip of the probe to a second position in the body cavity where the tip is positioned against body cavity tissue, and then determining that the tip is positioned against the body cavity tissue in a region of the body cavity which has previously been mapped, wherein a corresponding portion of the simulated surface has previously been marked as mapped on the display using a mapped visual design (x) indicating a first mapping resolution; and then
in an area of the simulated surface corresponding to said second position in the body cavity, replacing the mapped visual design (x) indicating the first mapping resolution with the different mapped visual design (y), the different mapped visual design (y) indicating a different and higher mapping resolution.

* * * * *